United States Patent
McCleary et al.

(10) Patent No.: US 6,949,101 B2
(45) Date of Patent: Sep. 27, 2005

(54) MEDICAL INSTRUMENT FOR MILLING A CURVED PATH IN BONE AND PROCEDURE

(75) Inventors: Larry G. McCleary, Warsaw, IN (US); Kimberly A. Dwyer, Wayne, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 198 days.

(21) Appl. No.: 10/113,171

(22) Filed: Mar. 29, 2002

(65) Prior Publication Data

US 2003/0187449 A1 Oct. 2, 2003

(51) Int. Cl.[7] .............................................. A61B 17/56
(52) U.S. Cl. ................................................... 606/80
(58) Field of Search ...................... 606/79–80, 84–86, 606/96

(56) References Cited

U.S. PATENT DOCUMENTS

| | | | |
|---|---|---|---|
| 4,328,839 A | * | 5/1982 | Lyons et al. ............... 138/120 |
| 4,706,659 A | | 11/1987 | Matthews et al. |
| 4,738,256 A | * | 4/1988 | Freeman et al. ............... 606/87 |
| 4,751,922 A | | 6/1988 | DiPietropolo |
| 4,777,942 A | | 10/1988 | Frey et al. |
| 4,790,852 A | | 12/1988 | Noiles |
| 5,203,595 A | | 4/1993 | Borzone et al. |
| 5,342,363 A | | 8/1994 | Richelsoph |
| 5,387,218 A | * | 2/1995 | Meswania .................... 606/80 |
| 5,468,243 A | | 11/1995 | Halpern |
| 5,527,316 A | | 6/1996 | Stone et al. |
| 5,540,694 A | | 7/1996 | DeCarlo et al. |
| 5,766,081 A | * | 6/1998 | Desmarais .................. 464/119 |
| 5,851,208 A | | 12/1998 | Trott |
| 5,908,423 A | | 6/1999 | Kashuba et al. |
| 6,053,922 A | | 4/2000 | Krause et al. |
| 6,106,528 A | * | 8/2000 | Durham et al. ............... 606/64 |
| 6,283,970 B1 | | 9/2001 | Lubinus |
| 2003/0027641 A1 | * | 2/2003 | Parsons ....................... 464/139 |

FOREIGN PATENT DOCUMENTS

| | | |
|---|---|---|
| FR | 2 708 462 | 2/1995 |
| GB | 2 250 441 A | 6/1992 |
| WO | WO 94/27507 | 12/1994 |

* cited by examiner

Primary Examiner—Eduardo C. Robert
(74) Attorney, Agent, or Firm—Magionot, Moore & Beck

(57) ABSTRACT

A medical instrument and procedure is adapted to mill bone along a curve and with respect to at least two angles of orientation with respect to an input source of rotary motion. Particularly, the medical instrument is a bone milling apparatus that is configured to mill bone along a predetermined curved path or curve. The bone milling apparatus includes a reamer that is rotatable about a curved shaft which is retained by a frame. The shaft has a predetermined curve that corresponds to a desired milling curve. The reamer is comprised of a plurality of interconnected segments, with each segment having cutting surfaces such that each segment is a cutter. The reamer is thus flexible with respect to the interconnection between the individual segments.

14 Claims, 11 Drawing Sheets the present invention relates to medical instruments and procedures and, more particularly, to a medical instrument capable of milling bone along a curve, especially in preparation for implantation of a prosthesis.

MEDICAL INSTRUMENT FOR MILLING A CURVED PATH IN BONE AND PROCEDURE

TECHNICAL FIELD OF THE INVENTION

The present invention relates to medical instruments and procedures and, more particularly, to a medical instrument capable of milling bone along a curve, especially in preparation for implantation of a prosthesis.

BACKGROUND OF THE INVENTION

For implantation of prosthetic stems, such as hip stems, accurate preparation of the bone or intramedullary canal is extremely important in order to guarantee good contact between the prosthesis stem and the bone. Preparation of the bone canal for implantation of a prosthetic stem is presently prepared by drilling a resected end of a bone, such as a femur, and then preparing an area adjacent the drilled hole to provide a seat for the prosthetic stem.

Preparation of the area adjacent the drilled hole may be accomplished by broaching or by milling. Currently, however, milling has been identified as an extremely precise method of bone preparation in many orthopaedic applications as compared to broaching. Bone milling is currently thus the preferred method of bone preparation. The concept is that a precise bone envelope reduces the gaps between the implant (i.e. prosthesis or prosthetic component) and the bone, thereby improving the initial and long-term bone ingrowth/fixation.

A critical limitation of milling systems today is that they use straight reamers to remove bone. Straight reamers limit the geometry that can be created in the bone and thus the external geometry of the corresponding implant. A typical milling frame can be seen in U.S. Pat. No. 5,540,694 issued to DeCarlo, J. et al. on Jul. 30, 1996. This milling frame uses a straight reamer that is useable for various geometries. For example, the anatomy of the medial endosteum of the femur can be described as a curve. Many implant designs thus employ a medial curve to load this region. It is therefore desirable to have a device that can precisely mill the bone to allow for the medial curve as such would improve the accuracy of the bone preparation and thus the bone fixation. One way of preparing the bone along a curved path is to use a series of broaches.

Broaches, however, have serious limitations. One such limitation is the risk of fracture during broaching. Since broaching is done by pounding the broach into the bone, the bone tends to fracture.

In consideration of the above, there have been attempts to provide flexible medullary canal reamers. Such medullary canal reamers are used to enlarge the medullary canal of bones in preparation for the insertion of a prosthetic component, such as a total hip prosthesis. One such device is provided in U.S. Pat. No. 6,053,922 issued to Krause et al. on Apr. 25, 2000. Krause describes a flexible shaft for a reamer. The Krause shaft comprises a solid element with a longitudinal bore the entire length thereof, and a slot formed thereon that extends spirally around the shaft either continuously or segmentally. A problem, however, with the Krause flexible shaft is that Krause is only concerned with the shaft portion and not the cutting portion of the reamer. As such, the cutting geometry associated with the reamer and the Krause flexible shaft is no different than other embodiment of reamers. As well, other flexible shafts fall short for the same reasons.

Additionally, prior reamers have fixed input shafts for connecting to and/or receiving motive (i.e. rotary) power. As such, the prior reamers are able to accept rotary input power with respect to only one direction. Typically, this direction is at 0° (i.e. "straight on"). Therefore, not only is the input power direction restricted, but this, in turn, restricts the angle at which the reamer may be used on a patient.

In view of the above, it would be desirable to have a bone miller or guided reamer for preparing non-axisymmetric bone.

It would be further desirable to have a bone cutter that can mill complex bone geometries.

It would be still further desirable to have a bone cutting device that can mill bone along a curve, especially a curve of any radius of curvature.

It would be yet further desirable to have a bone cutter that can provide precise milling along any defined curve.

It would be even farther desirable to have a bone milling device as desired above that also is able to accept input rotary power from various angular orientations and/or allows bone milling device to be positioned at various angular orientations relative to the input rotary power.

SUMMARY OF THE INVENTION

The subject invention is a bone milling apparatus that is configured to mill bone along a curve. The subject invention also provides a procedure of use for the bone milling apparatus.

The bone milling apparatus comprises a frame, a flexible reamer, and a guide for the flexible reamer, and an input coupled to the flexible reamer that is adapted to be coupled to a rotary motion input. The guide has a predetermined curve. The flexible reamer includes a plurality of cutters that are linked to each other and carried by the guide so as to be rotatable thereon. The input allows the flexible reamer to be positioned in two or more angular orientations relative to the rotary motion input.

In one form, the subject invention provides a reamer for milling bone. The reamer includes a plurality of individual, interlocking segments, with each segment including a cutting surface, and a multi-orientation input coupling in communication with a first one of said plurality of segments and configured to be coupled to a source of rotary motion. The multi-orientation input coupling is configured to transmit rotary motion from the source of rotary motion to the plurality of segments.

In another form, the subject invention provides a reamer for milling bone. The reamer includes a first segment, a last segment configured to be rotatably received in a milling frame, a plurality of intermediate segments defining a first end that is linked to the first segment and a second end that is linked to the last segment with each intermediate segment having a first cutting surface. The reamer further includes an input coupling in communication with the first segment and configured to be coupled to a source of rotary motion. The input coupling allows two angles of orientation of the reamer with respect to the source of rotary motion.

In yet another form, the subject invention provides an apparatus for milling bone. The bone milling apparatus includes a frame, a curved guide supported by the frame, a reamer rotatably maintained on the curved guide the reamer comprising a plurality of linked segments with each linked segment having a cutting surface. The bone milling apparatus further includes a multi-orientation input coupling in communication with a first one of the plurality of segments and configured to be coupled to a source of rotary motion. The multi-orientation input coupling configured to transmit rotary motion from the source of rotary motion to the plurality of segments.

In a still further form, the subject invention provides an apparatus for milling bone including a frame, a curved guide supported by the frame, and a reamer rotatably maintained on the curved guide. The reamer includes a first segment, a last segment configured to be rotatably received in a milling frame, and a plurality of intermediate segments defining a first end that is linked to the first segment and a second end that is linked to the last segment, each intermediate segment having a first cutting surface. The bone milling apparatus further includes an input coupling in communication with the first segment and configured to be coupled to a source of rotary motion, the input coupling allowing two angles of orientation of the reamer with respect to the source of rotary motion.

In still yet another form, the subject invention provides a method of preparing a bone for prosthetic implantation. The method includes the steps of: (a) resecting a portion of a bone; (b) reaming the intramedullary canal of the bone; and (c) milling an area of the bone adjacent the reamed intramedullary canal using a flexible reamer coupled to a source of rotary motion at a first angle of orientation relative to the source of rotary motion and then at a second angle of orientation relative to the source of rotary motion.

In an even further form, the subject invention provides a medical instrument kit for milling bone. The medical instrument kit includes a frame, a plurality of guide shafts each of which is adapted to be carried by the frame, each guide shaft having a different radius of curvature, a reamer rotatably maintained on the guide shaft, the reamer comprising a plurality of linked segments, each linked segment having a cutting surface, and a multi-orientation input coupling in communication with a first one of the plurality of segments and configured to be coupled to a source of rotary motion, the multi-orientation input coupling configured to transmit rotary motion from the source of rotary motion to said plurality of segments, wherein the frame is adapted to removably receive one of the plurality of guide shafts.

The subject invention allows a user to mill bone along a predetermined curve or curved path. Milling is preferred over broaching since milling decreases the gap between implant and bone which is critical for long term fixation. The subject invention provides the ability to mill complex, curved geometry that allows better loading of the nearby bone being milled.

Additionally, the subject invention allows the flexible reamer to be used in two or more, and preferably a plurality, of angular orientations relative to a source of rotary motion/power input and/or coupled thereto.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

Figure 1:
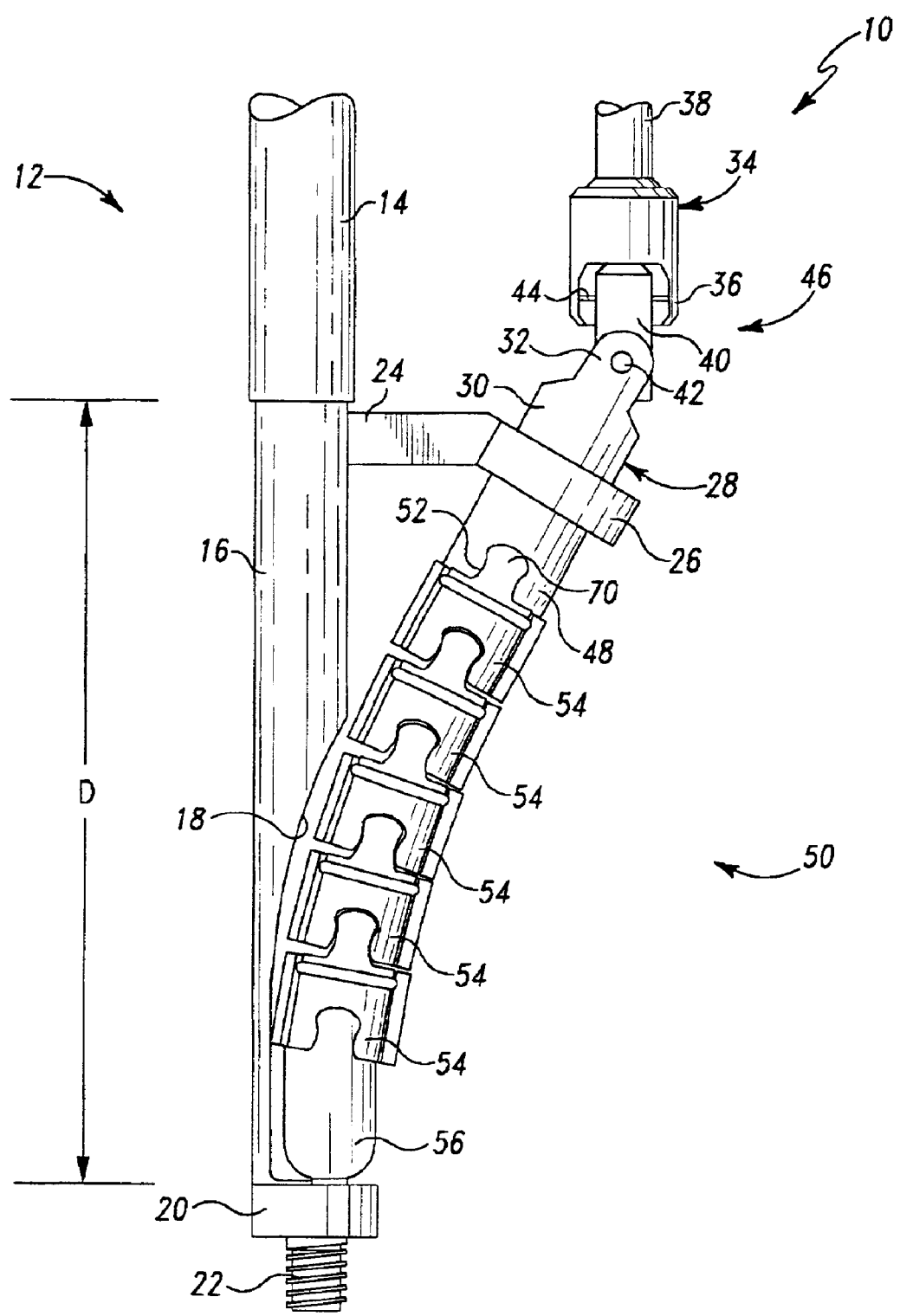
FIG. 1 is a side view of an exemplary bone milling apparatus in accordance with the principles of the subject invention.

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring now to FIG. 1 there is shown a side view of an exemplary embodiment of a bone milling apparatus generally designated 10. The bone milling apparatus 10 includes a frame, support, guide, or the like generally designated 12. The frame 12 includes a first or upper portion 14 here constituting a tube, shaft, tubular member, rod, or the like, and a second or lower portion 16 here constituting a tube, shaft, tubular member, rod, or the like, that may be smaller in diameter than the upper portion 14 or may be the same diameter. The cross-sectional shape of both the upper and lower portions 14 and 16 may be the same or different, and may be circular, rectangular, or any other suitable shape. Preferably, the upper and lower portions 14 and 16 are made from stainless steel but other suitable materials may be used as appropriate.

The lower portion 16 of the frame 12 has a base 20 with a connector 22 extending axially therefrom. While not shown in FIG. 1, a guide is adapted to be coupled to the connector 22. As such, the connector 22 is shown (embodied as) a threaded shaft but can be any type of connector. The guide is configured to extend into a previously reamed intramedullary canal of a bone. The lower portion 16 further has a curved cutout or notch 18 along one side of thereof. The notch 18 extends from a point on the lower portion 16 to the base 20. The notch 18 has a curvature that corresponds to the curvature of a reamer 50.

An arm 24 extends substantially perpendicular to the upper and lower portions 14 and 16 and is preferably, as shown, but not necessarily, coupled to the lower portion 16. The arm 24 supports a yoke or ring 26. The yoke 26 is preferably angled downwardly with respect to the arm 24 so that the reamer 50 substantially forms a hypotenuse of a triangle along with the arm 24 and the lower portion 16. The yoke 26 retains or holds a drive connector 28. The drive connector 28 is rotatable within the yoke 26.

The drive connector 28 has a top portion 30 terminating in a U-member 32. The U-member 32 is adapted to be coupled to standard reamer power driver equipment (not shown in FIG. 1), through a input coupling 34. The input coupling 34 also includes a U-member 36 at one end and a drive shaft 38 at another end. The drive shaft 38 is adapted to be coupled to the standard reamer power driver or other rotary motive devices.

A drive interface 40 provides an interface between the input coupling 34 and the drive connector 28. The drive connector 28 and the input coupling 34 define an interface coupling 46 that couples rotation of the input coupling 34 to the drive connector 28. The drive interface 40 is situated in the U-member 32 and is connected thereto by a pivot pin 42. In like manner, the drive interface 40 is situated in the U-member 36 and is connected thereto by a pivot pin 44. In this manner the input coupling 34 and the drive connector 28 define a multi-orientation input joint/coupling 46 such as a universal joint. This allows the reamer power driver (or other rotary motive device) to be oriented in various positions during the milling process and/or vice versa. It should be appreciated that the multi-orientation input joint/coupling 46 may take different forms. A criterion is for the input coupling 34 to be operative to transfer rotary motion to the drive connector 28.

Figure 7A:
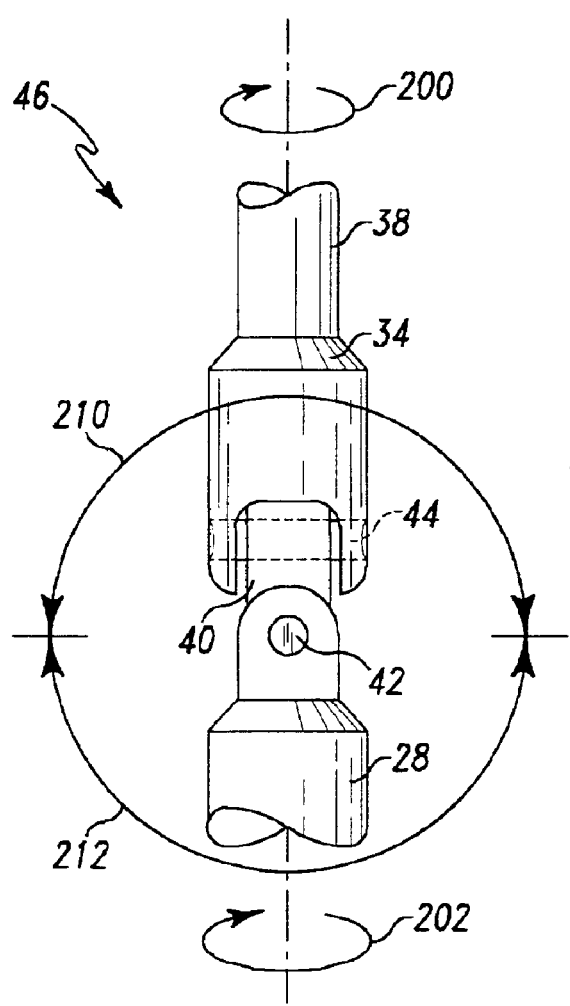
FIGS. 7A and 7B are enlarged front views of the coupling between the reamer of the bone milling apparatus and a source of rotary motion/power.
Figure 7B:
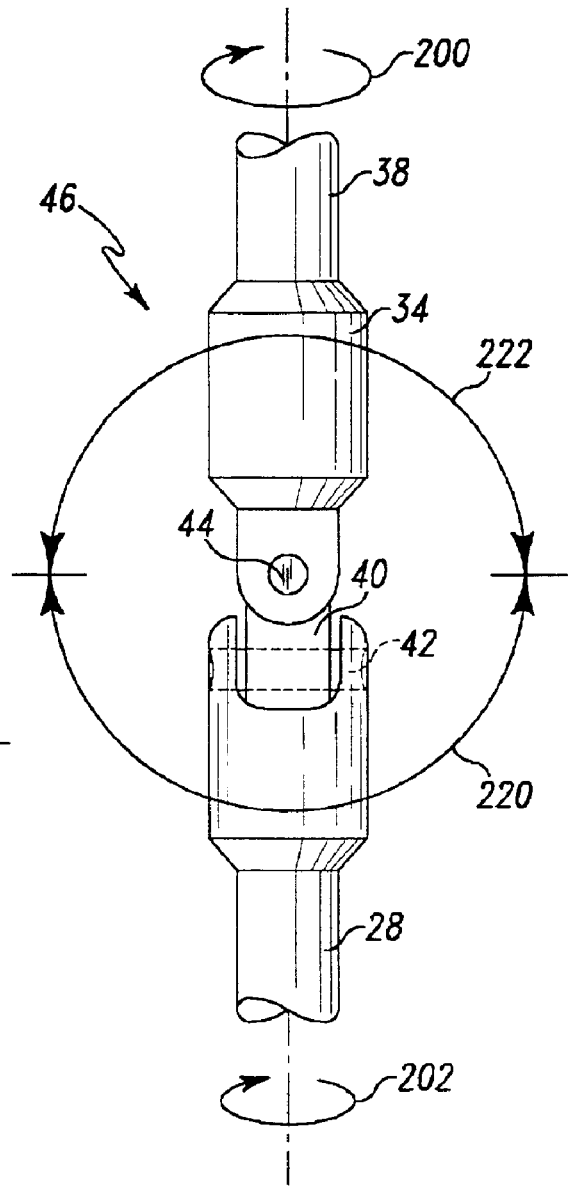

Referring to FIGS. 7A and 7B, the multi-orientation input joint/coupling 46 will be described in greater detail. Initially, it should be appreciated that the multi-orientation input joint/coupling 46 may allow from only two angle of input/reaming to an infinite number of angles of input/reaming along a continuous path of movement. As depicted in FIGS. 7A and 7B, the input coupling 34 is adapted to rotate as indicated by the arrow 200. While the arrow 200 indicates a particular direction of rotation, and only one direction, it should be appreciated that the input coupling 34 may be rotated in the opposite direction. Since the input coupling 34 is coupled to the drive connector 28 via the drive interface 40, the drive connector 28 likewise rotates in the direction of rotation of the input coupling 34 as indicated by the arrow 202.

The drive interface 40 and thus the input coupling 34 are connected to the drive connector 28 via the pivot pin or hinge 42. In accordance with one perspective and specifically referring to FIG. 7A, the input coupling 34 and the drive interface 40 pivots about the pivot pin 42 and the drive coupling 28 as indicated by the arrow 210. If the drive connector 28 is held stationary, the input coupling 34 and the drive interface 40 are able to pivot about the pivot pin 42 in a 180° arc as represented by the arrow 210. Thus, the rotary motion device (not shown in FIG. 7A) may be positioned in various angular orientations while the reamer 50 is held stationary.

In accordance with another perspective and again specifically referring to FIG. 7A, the drive coupling 28 pivots about the pivot pin 42, the input coupling 34 and drive interface 40 as indicated by the arrow 212. If the input coupling 34 is held stationary, the drive coupling 28 and the drive interface 40 are able to pivot about the pivot pin 42 in a 180° arc as represented by the arrow 212. Thus, the rotary motion device may be held stationary while the reamer 50 may be positioned in various angular orientations.

In accordance with another perspective and specifically referring to FIG. 7B, the input coupling 34 pivots about the pivot pin 44, the drive interface 40 and the drive coupling 28 as indicated by the arrow 222. If the drive connector 28 is held stationary, the input coupling 34 is able to pivot about the pivot pin 44 in a 180° arc as represented by the arrow 222. Thus, the rotary motion device (not shown in FIG. 7B) may be positioned in various angular orientations while the reamer 50 is held stationary.

In accordance with another perspective and again specifically referring to FIG. 7B, the drive coupling 28 and the drive interface 40 pivots about the pivot pin 44 and the input coupling 34 as indicated by the arrow 220. If the input coupling 34 is held stationary, the drive coupling 28 and the drive interface 40 are able to pivot about the pivot pin 44 in a 180° arc as represented by the arrow 220. Thus, the rotary motion device may be held stationary while the reamer 50 may be positioned in various angular orientations.

Figure 2:
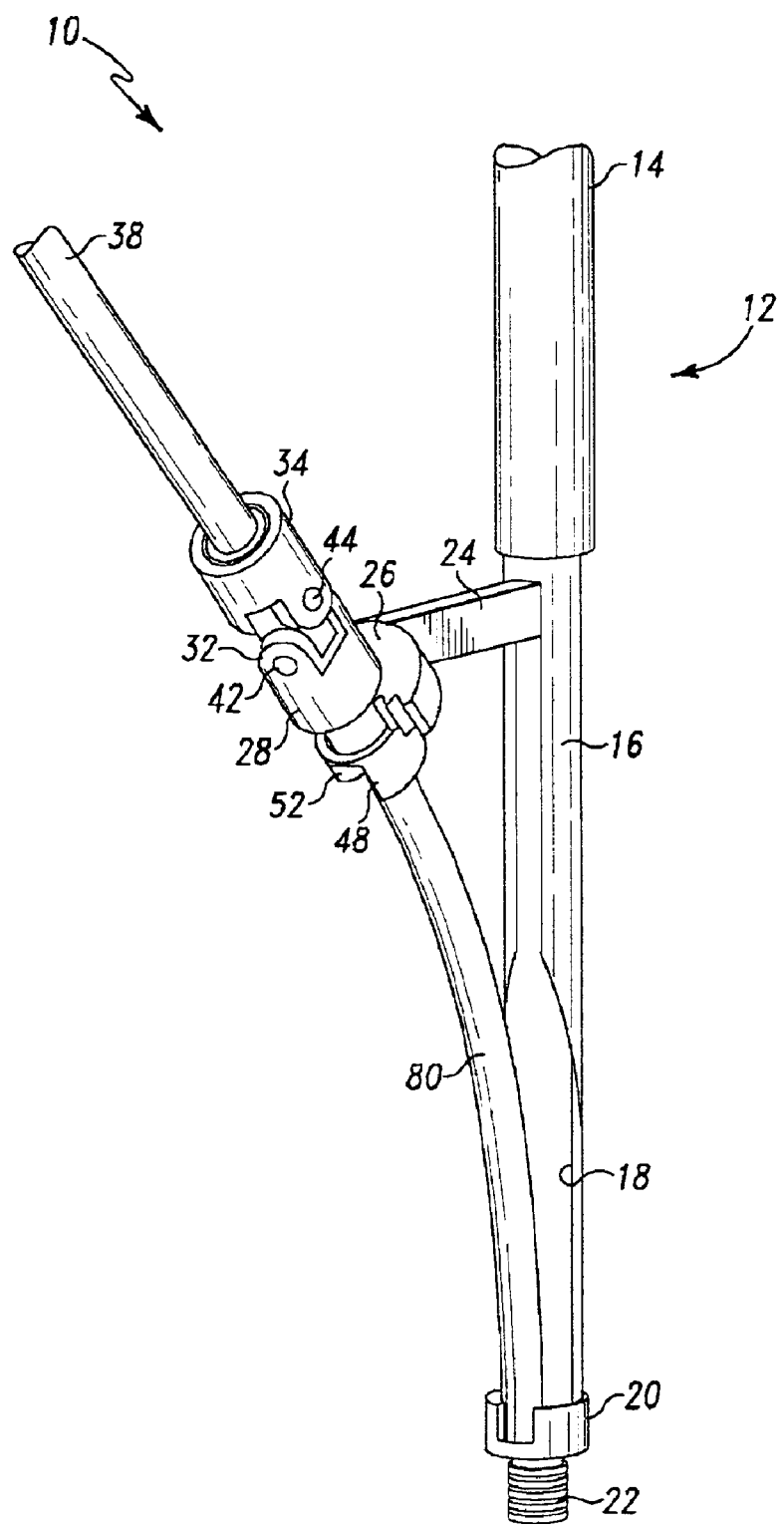
FIG. 2 is a perspective view of the exemplary bone milling apparatus of FIG. 1 with its cutting segments removed showing its curved guide shaft.
Figure 3:
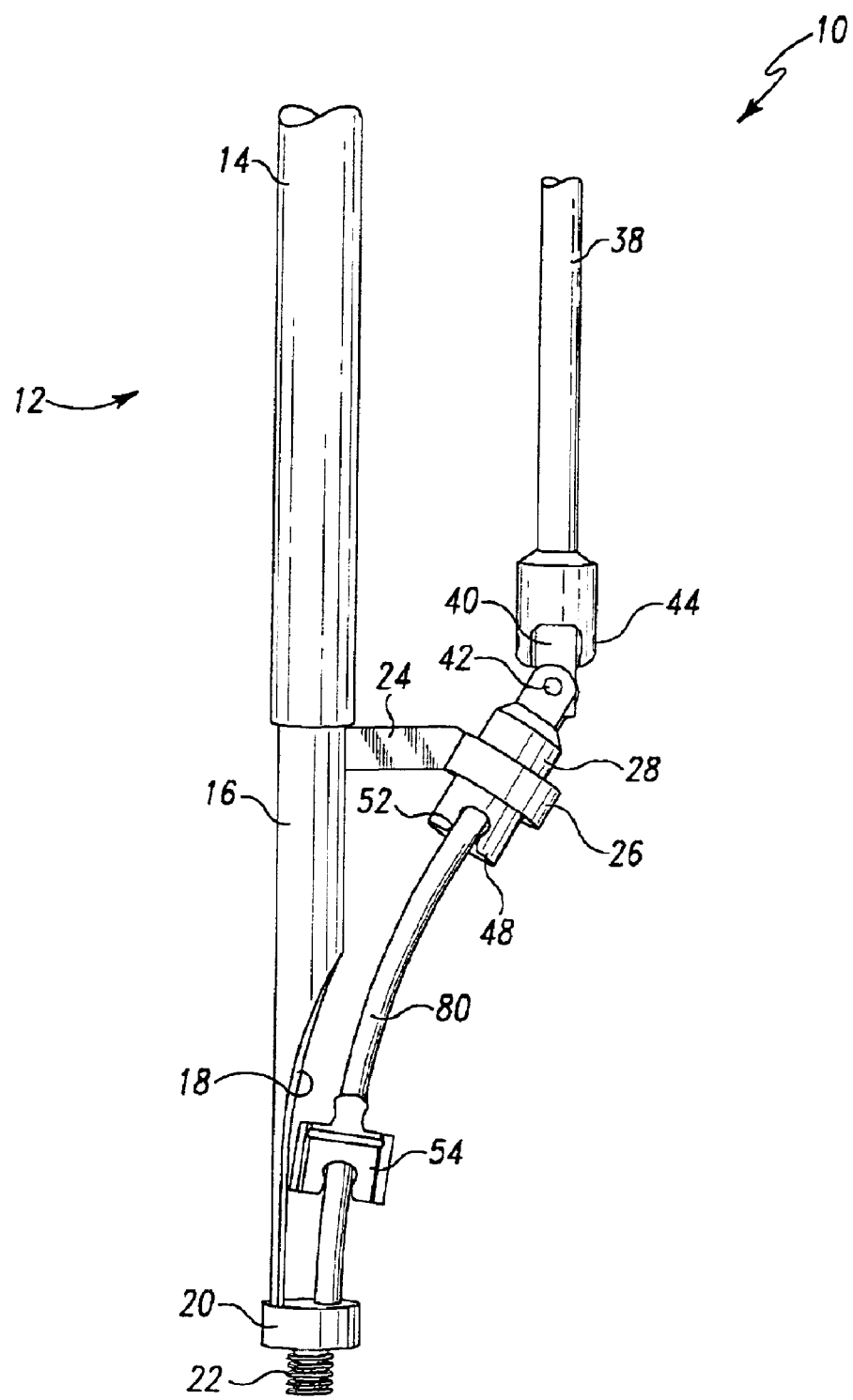
FIG. 3 is a side view of the exemplary bone milling apparatus of FIG. 1.

The drive connector 28 defines a bottom portion 48 that has a receptor 52, here embodied as a mortise, concavity or like (see e.g., FIGS. 2 and 3). The mortise 52 is configured and/or adapted to receive and/or allow connection with the reamer 50. In this manner, rotation of the drive connector 28 rotates the reamer 50. The reamer 50 is configured, adapted, and/or operative to mill bone matter as it is extended into a bone. This will be explained further in connection with an exemplary procedure utilizing the subject exemplary bone milling apparatus 10.

The reamer 50 consists of a plurality of segments, cutters, cutting elements, cutting segments, or the like 54 and a termination segment 56. The cutting segments 54 are linked and/or coupled to one another and extend from the drive connector 28 to the termination segment 56. The cutting segments 54 are linked to provide flexibility to the reamer 50 and/or allow the reamer 50 to bend or curve. Additionally, the cutting segments 54 and the termination segment 56 are rotatable in the curved position. The reamer 50 may consist of as many cutting segments 54 as appropriate. As detailed below, the reamer 50 may be formed into any curve, radius of curvature (rate of curve) or the like.

Figure 4:
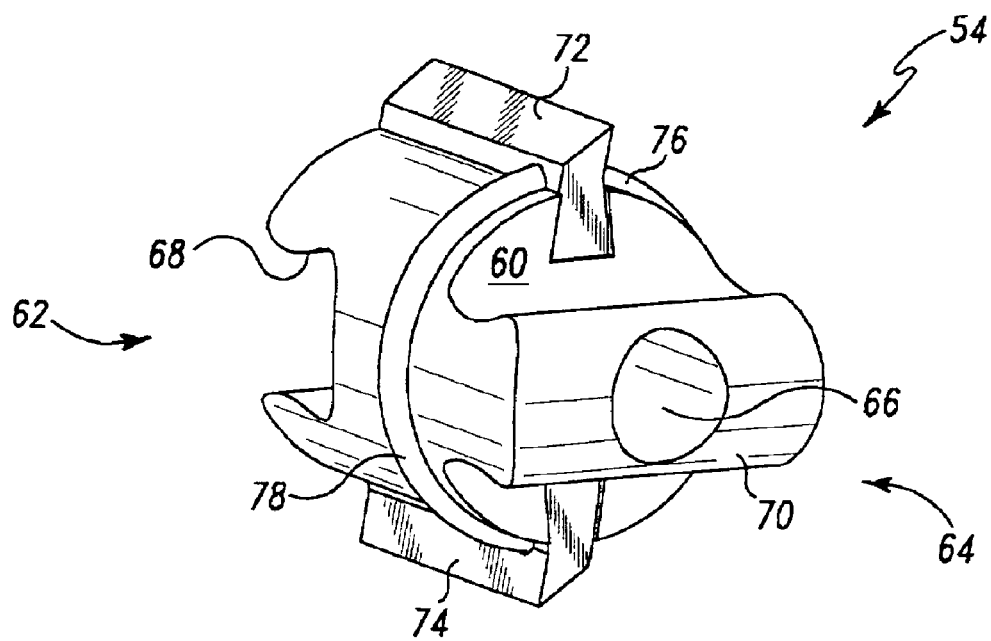
FIG. 4 is a bottom perspective view of a cutting segment of the bone milling apparatus of FIG. 1.
Figure 5:
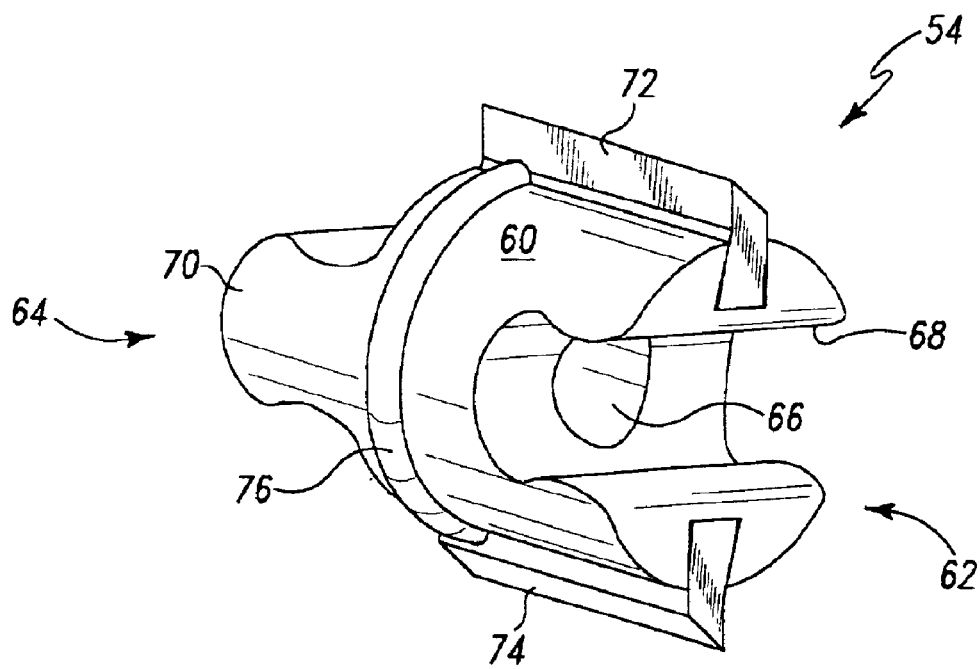
FIG. 5 is a top perspective view of the cutting segment.
Figure 6:
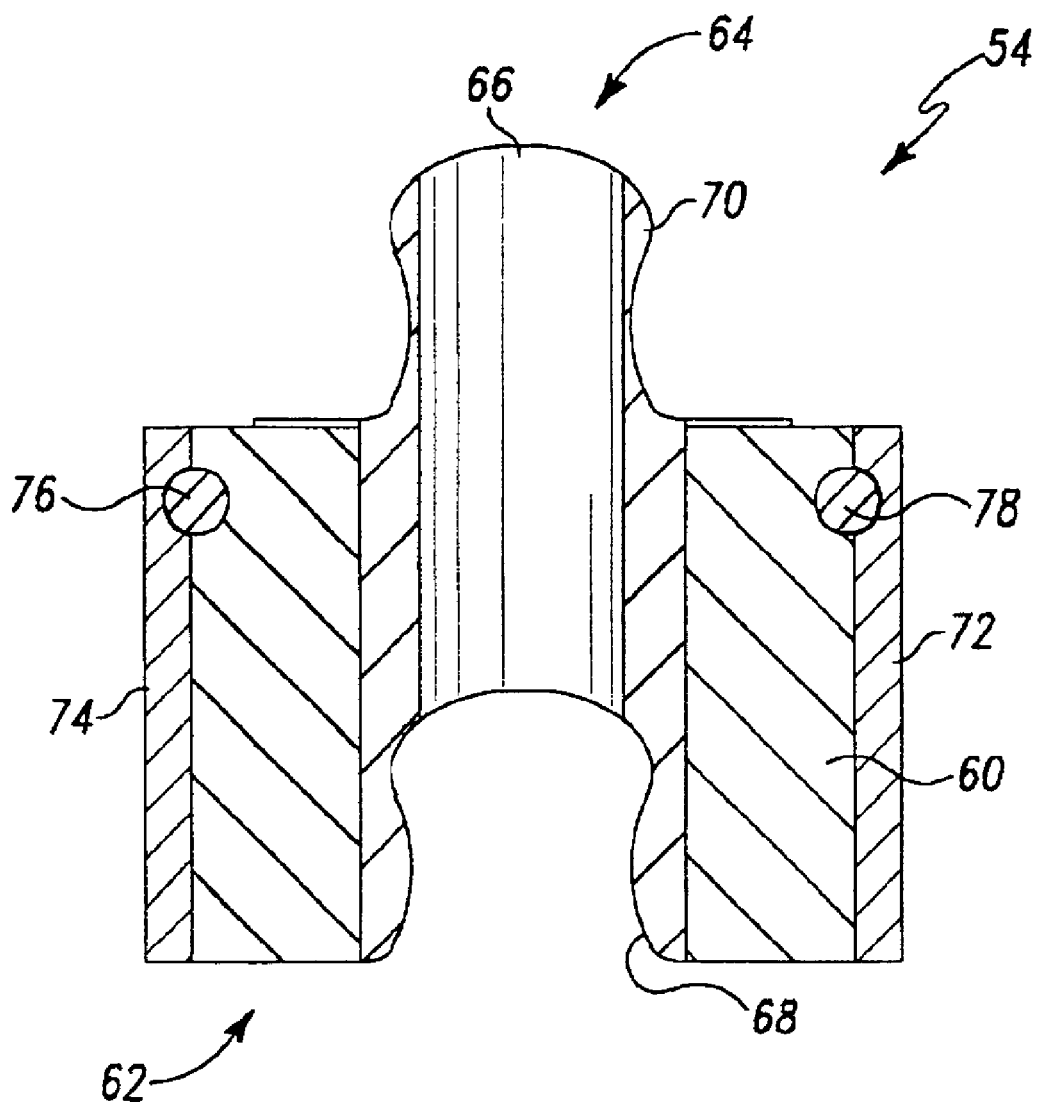
FIG. 6 is a sectional view of the cutting segment taken along line 6—6 of FIG. 4.

With reference to FIGS. 4–6, a cutting segment 54 will be described. It should be appreciated that each cutting segment 54 is preferably identical or at least substantially identical in shape, but not necessarily in size (e.g. diameter) with one another. Therefore, the cutting segment 54 shown in FIGS. 4–6 represents each cutting segment 54 of the reamer 50. It should, however, be appreciated that the cutting segments may differ from one another if desired. Variations may be used for various purposes.

The cutting segment 54 is defined by a body 60 preferably formed of stainless steel or other appropriate material. The body 60 is preferably substantially cylindrical but may take any other suitable shape, depending on the desired shape of a bore resulting from milling by the reamer 50/cutting segments 54. The body 60 has a first end 62 and a second end 64 each of which is named arbitrarily. A cannula, bore or hole 66 extends preferably centrally through the body 60. The cannula 66 is sized to extend about a shaft such that the body 60 is retained on the shaft. The cannula 66 defines an axis of rotation of the cutting segment 54.

The first end 62 has a mortise, concavity or concave structure 68 while the second end has a tenon, convexity or convex structure 70. The mortise 68 extends generally perpendicular to the cannula/axis of rotation 66. The tenon 70 likewise extends generally perpendicular to the cannula/axis of rotation 66. The mortise 68 and tenon 70 are complementary in structure such that a tenon 70 of another cutting segment 54 is receivable in the present mortise 68 and, a mortise 68 of another cutting segment 70 receives the present tenon 70. In this manner, the cutting segments 54 are linked to one another. Such linking allows the reamer 50 to be of any length and flexible. Such flexibility exists because of a pivoting motion between the mortise or concavity and the tenon or convexity. It should be appreciated that structures other than those depicted for the concavity and the convexity may be utilized and is contemplated.

The body 60 also includes a first cutting tooth, blade, structure, feature, surface or the like 72 and a second cutting tooth, blade, structure, feature, surface, or the like 74. Each cutting surface 72 and 74 extends longitudinally along the outside of the body 60 and a distance axially therefrom. A diameter from axial tips of the cutting surfaces 72 and 74 determines the diameter of the milled portion of the bone. Thus, not only does the diameter of the body 60 determine the diameter of the milled portion of the bone, but the axial lengths of the cutting teeth. Additionally, the first and second surfaces 72 and 74 are disposed diametrically opposite one another.

It should also be appreciated that while only two cutting surfaces are shown, the cutting segment 54 may have only one cutting surface, or may have more than two cutting surfaces. Regardless of the number of cutting surfaces, in a preferred embodiment, each cutting surface is configured to mill bone in a single rotational direction. It should be appreciated, while not shown, that cutting surfaces may be provided that allow cutting in both rotational directions. It should also be appreciated that as an alternative embodiment, the mortise and tenon of the body 60 may be reversed and/or that each cutting segment 54 of the reamer 50 maybe flipped 180°.

Further, rather than each cutting surface comprising a single elongated, axially straight cutter, each cutting surface may consist of several, separate surfaces that may be straight or curved. Alternatively, a plurality of surfaces may be provided that are straight, curved, spiraled, or a combination thereof. Various combinations and/or configurations of cutting surfaces are contemplated.

Referring back to FIG. 1, with respect to the reamer 50, a first cutting segment 54 thereof is coupled to the lower portion 48 of the drive connector 28. Particularly, the tenon 70 of the first cutting segment 54 is linked to the mortise 52 of the lower portion 48 via the drive connector 28. A second cutting segment 54 is in like manner coupled or linked to the first cutting segment 54 in essentially axial alignment therewith. A given number of cutting segments 54 are then linked to each other in substantially axial alignment with one another with a last cutting segment 54 linked to the end or termination segment 56. The number of cutting segments 54 of the reamer 50 is determined by the length of each cutting segment 54 and the overall length of the guide shaft 80. Additionally, each cutting segment 54 may have the same diameter (i.e. 10 mm), several cutting segments 54 may have the same diameter while others may have a different diameter, each cutting segment 54 may be different in diameter, or other various combinations. If each cutting segment has a different diameter, the diameters preferably increase from a beginning of the reamer (distal the input connector) to the end of the reamer (proximate the input connector).

Figure 12:
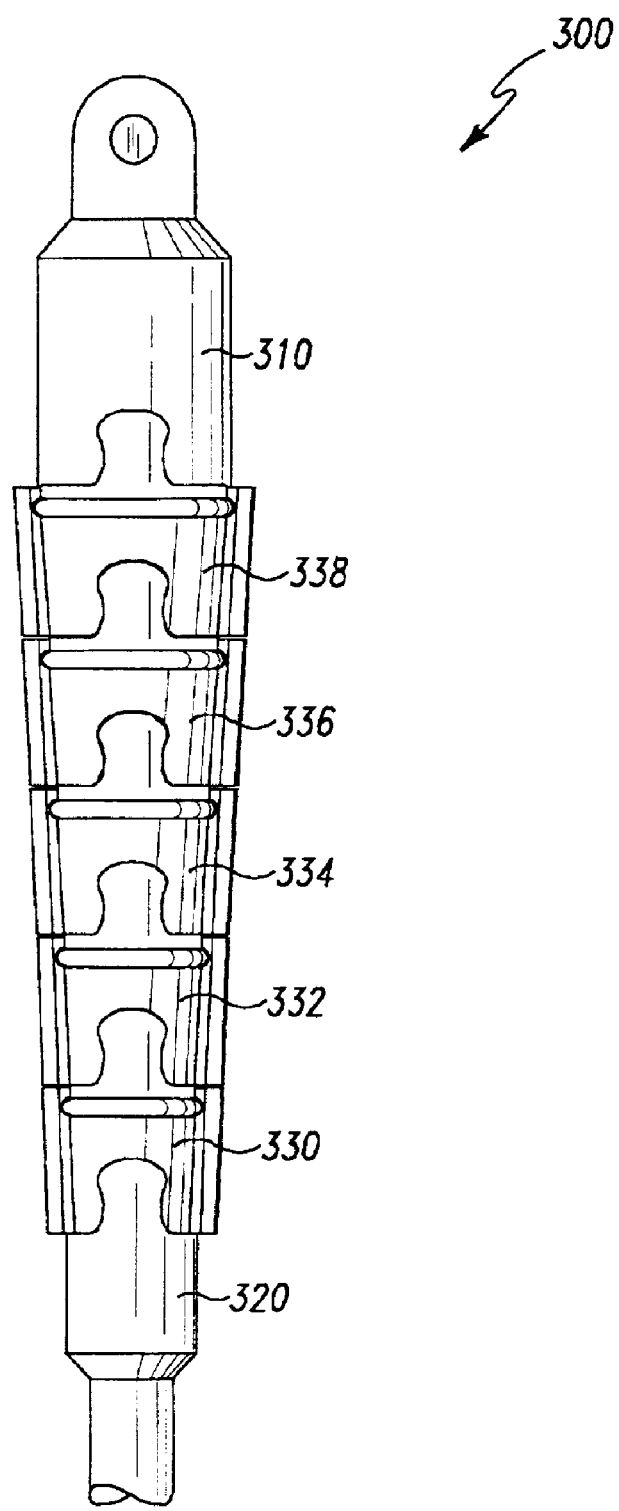
FIG. 12 is a side view of an alternative embodiment of a reamer in accordance with an aspect of the subject invention.

Referring to FIG. 12, an alternative embodiment of a reamer, generally designated 300 is depicted. The reamer 300 has an input connector segment 310 and an ending segment 320 both of which are in like manner to the other embodiments. In this embodiment, however, the reamer 300 forms a cone wherein the cutting segment 330 is smaller in diameter than an adjacent cutting segment 332, which is smaller in diameter than an adjacent cutting segment 334, which is smaller in diameter than an adjacent cutting segment 336, which is smaller in diameter than an adjacent cutting segment 338. Of course any number of cutting segments may make up the reamer 300.

Referring now to FIGS. 2 and 3, the bone milling apparatus 10 is shown with most or all of the cutting segments 54 removed to illustrate that the bone milling apparatus 10 further includes a guide in the form of a shaft 80. The shaft 80 is provided in a predetermined curve that extends from the drive connector 28 to the base 20. The rate of curvature between distance D from the yoke 26 to the base 20 (see FIG. 1) is determined based on the desired amount of bone to be milled and/or the desired geometry of the bone area to be milled. Thus, the shaft 80 provides a guide curve for milling by the reamer 50. The shaft 80 is stationary with respect to the cutting segments 54 (reamer 50) that rotate about the shaft 80. Each cutting segment 54 is situated on the shaft 80. Particularly, each cutting segment 54 is rotatably retained on the shaft 80. The shaft 80 extends through the bore 66 of the body 60 of the respective cutting segment 54. As well, all of the cutting segments 54 rotate in unison which constitute the reamer 50.

According to one aspect of the subject invention, the frame 12 is operative to support shafts of different lengths and/or curvatures. These shafts are replaceable within the frame 12 preferably in a modular fashion. The cutting segments 54 are interchangeable with the various shafts, that is the cutting segments 54 may be used with any of the various shafts.

It should be appreciated that the shaft 80 determines the curve of the reamer 50. Since the reamer 50 is comprised of a plurality of cutting segments, the reamer 50 can bend or curve and is thus flexible. As such, the shaft 80 that retains the plurality of cutting segments 54 may be of any curvature. The present bone milling apparatus 10 may thus be part of a kit in which shafts of various curves and/or rate of curvature are supplied along with a number of cutting segments. Curve guide cartridges (modular or replaceable shafts) may be provided that are accepted by the frame 12. In this manner a family of curves of varying radii may be supplied and used.

Use of the Subject Invention

Figure 8:
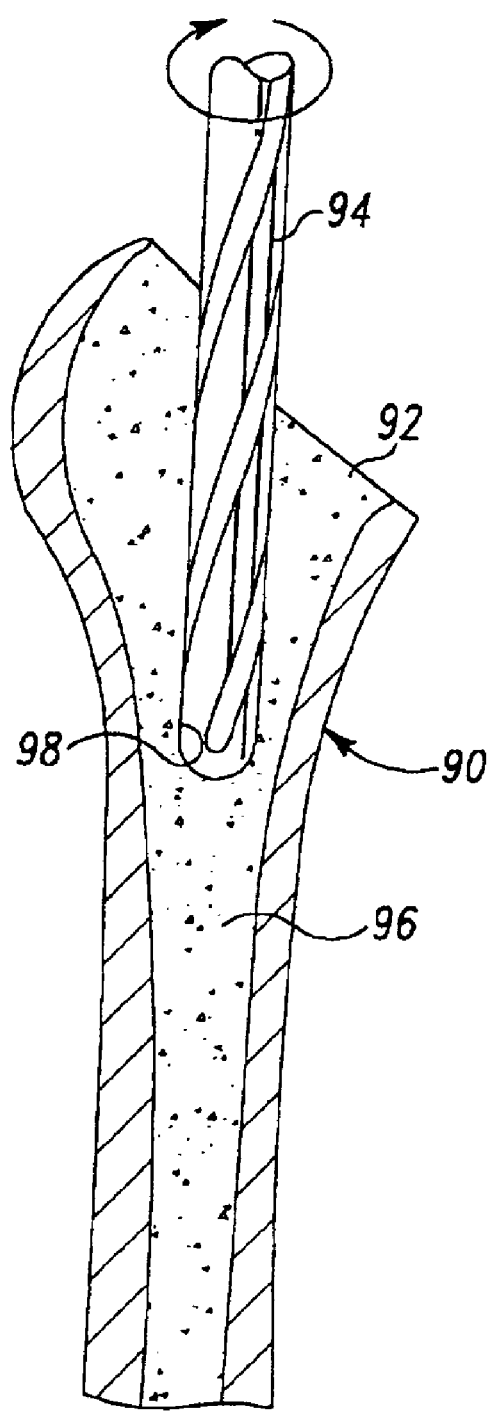
FIG. 8 is a side sectional view of a portion of a resected femur being initially prepared for prosthetic implantation.

A use and/or application of the subject invention will now be described. It should be appreciated, however, that the below-described use/application of the subject invention is only exemplary of one manner of use. Other manners of use not specifically described herein are contemplated. Referring to FIG. 8, there is depicted a femur (in cross-section) generally designated 90 that has been initially prepared for implantation of a prosthetic. Particularly, a top portion of the femur 90 has been resected to provide a resected surface 92. Such resection is accomplished as is known in the art for the particular prosthesis to be implanted. After resection, the intramedullary canal 96 is drilled to create a bore 98. A standard reamer 94 is shown making the bore 98 in the intramedullary canal 96. Of course, other manners of providing a bore 98 in the intramedullary canal 96 may be used.

Figure 9:
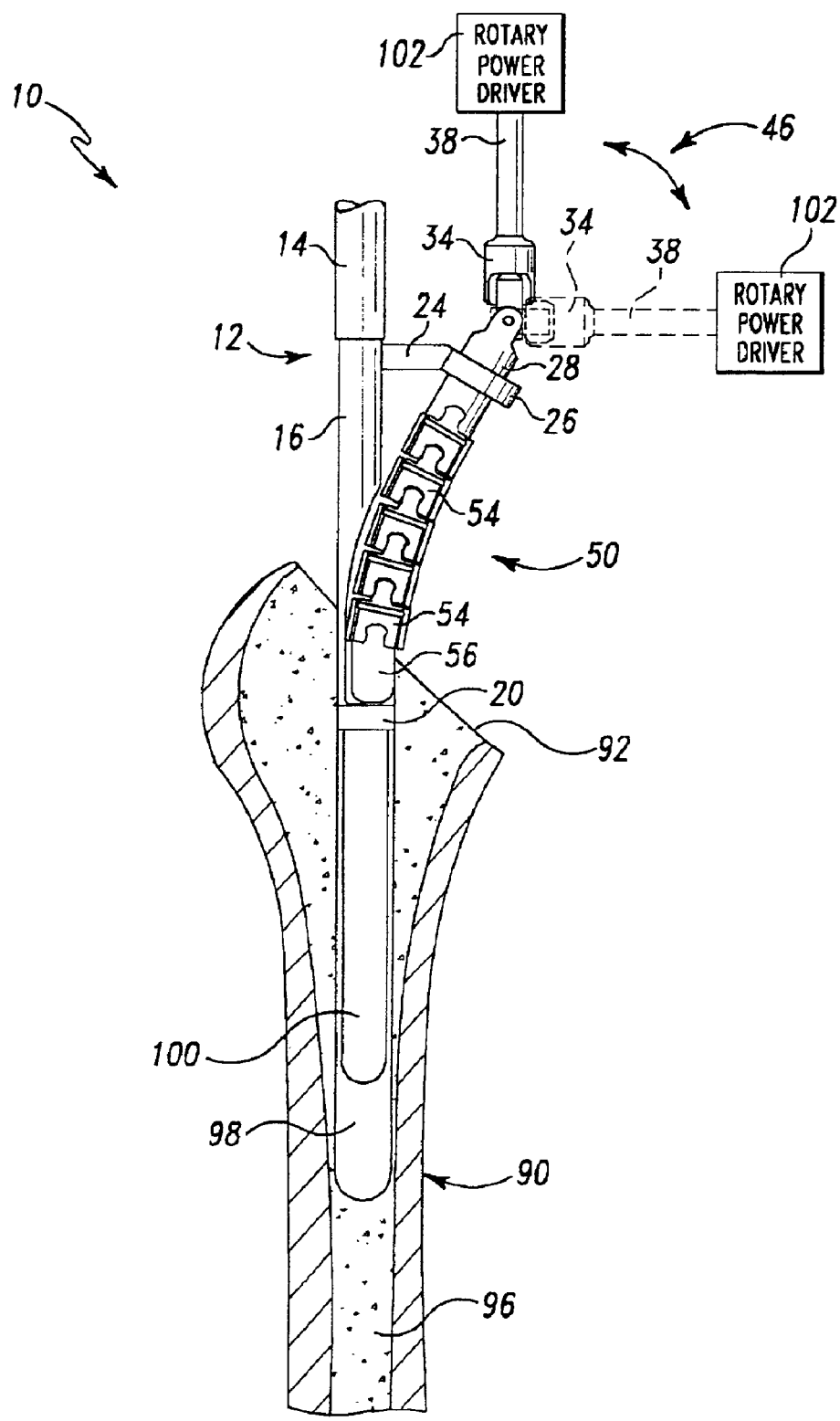
FIG. 9 is a side sectional view of the exemplary bone milling apparatus initially milling the initially resected femur of FIG. 8.

Referring to FIG. 9, the bore 98 has been reamed or drilled completely into the intramedullary canal 96. The length or depth of the bore 98 is dependent upon the implant and/or other factors that are not necessary to be detailed for the present application. FIG. 9 depicts the next step which is to advance the bone milling apparatus 10 into the femur 90. Attached to the milling apparatus 10 is a guide 100. Particularly, the guide 100 is threadedly attached to the connector 22 prior to initial insertion of the bone milling apparatus 10. The guide 100 is placed in the bore 98 as the bone milling apparatus 10 is placed downwardly into the femur 90.

The bone milling apparatus 10 is coupled to a power driver 102 that is operative to provide motive rotary power. Particularly, the shaft 38 is coupled to the rotary power driver 102 such that shaft 38 rotates the coupling 28 which, in turn, rotates the drive connector 28. Rotation of the drive connector 28 rotates the reamer 50 about the shaft 80. As the reamer 50 is rotated, the bone milling apparatus 10 is advanced into the femur 90. The cutting teeth of each cutting segment 54 mills bone during advancement. FIG. 9 depicts the rotary power device 102 in various positions to illustrate the nature of the multi-orientation joint/coupling 46. Of course, as indicated above, the rotary power device 102 may be held stationary while the milling device 10 may be positioned in various angular orientations.

Figure 10:
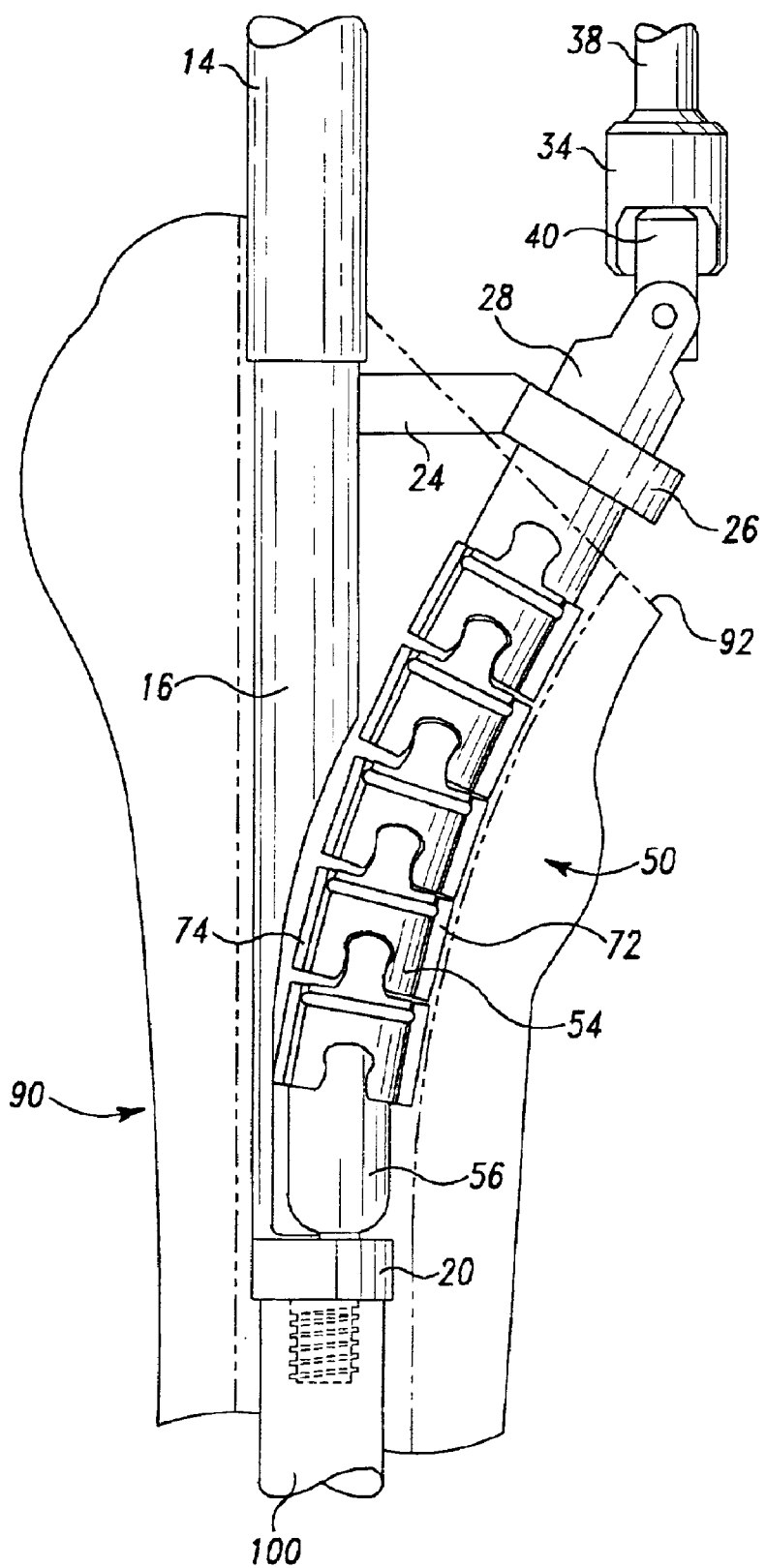
FIG. 10 is a side sectional view of the exemplary bone milling apparatus completing the milling process.

Referring to FIG. 10, the bone milling apparatus 10 is shown advanced into the femur 90 such that the reamer 50 has milled a substantially triangular area in the femur 90 and/or when the curve substantially matches the patient's bone anatomy. Typically, the bone milling apparatus 10 is advanced into the femur 90 until the yoke 26 is proximate the resection surface 92 and/or the milled curve matches the medial endosteum.

Figure 11:
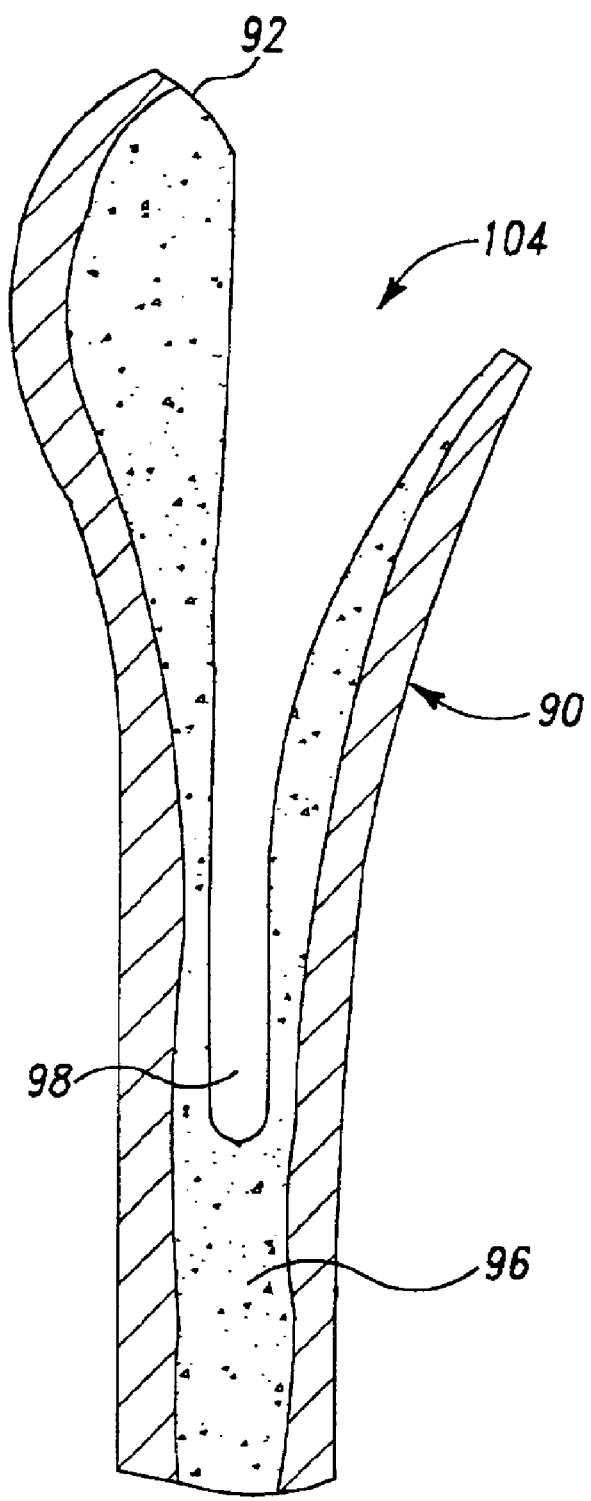
FIG. 11 is a side sectional view of the prepared femur of FIG. 10 ready for prosthetic implantation.

FIG. 11 depicts the prepared femur 90 in which an area 104 has been prepared (milled) by the bone milling apparatus 10. The prepared area 104 (triangular area) is ready to receive the implant (not shown).

The subject invention provides various features and/or advantages. For example, the subject invention provides interlocking cutting segments that exist within a generally cylindrical geometry when the bone milling apparatus 10 is in a rest state. The reamer 50 of the bone milling apparatus 10 is flexible and cannulated. Such flexibility can accommodate a range of guide curves (shafts) that are consistent with an associated implant geometry that a user is duplicating in bone preparation. The entire length of the flexible reamer 50 provides cutting or milling of bone and can be driven by standard reamer driver power equipment. Since the reamer 50 is comprised of a plurality of individual segments, an individual segment can be replaced when dull. This obviates the need to replace the entire reamer. Functionality of the subject bone milling apparatus 10 can be extended from use with respect to a single type of implant to use for a plurality of implants through the use of different shafts 80. Each shaft would have different curves or shafts of varying radii. Such would be provided in a kit. As well, the kit may provide a plurality of sets of cutting segments, with each set of cutting segments of a particular diameter. For example, one set of cutting segments may have a cutting diameter of 9 mm, while another set of cutting segments may have a cutting diameter of 25 mm. Sets of a range of cutting diameter segments from 9 mm to 27 mm, for example, in 1.5 mm to 2.0 mm increments may be provided as well. Different cutting diameter cutting segments may also be mixed and matched if desired. Various combinations are contemplated.

There is a plurality of advantages of the subject invention arising from the various features of the bone milling apparatus described herein. It will be noted that alternative embodiments of the bone milling apparatus of the subject invention may not include all of the features described yet still benefit from at least some of the advantages of such features. Those of ordinary skill in the art may readily devise their own implementations of a bone milling apparatus that incorporate one or more of the features of the subject invention and fall within the sprit and scope of the subject invention.

What is claimed is:

1. An apparatus for milling bone comprising:
   a frame;
   a curved guide supported by said frame;
   a reamer rotatably maintained on said curve guide, said reamer comprising a plurality of linked segments, each said linked segment having a cutting surface; and
   a multi-orientation input coupling in communication with a first one of said plurality of segments and configured to be coupled to a source of rotary motion, said multi-orientation input coupling configured to transmit rotary motion from the source of rotary motion to said plurality of segments,
   wherein said multi-orientation input coupling comprises a drive connector that is removably coupled to said first one of said plurality of segments whereby said drive connector may be decoupled from said first one of said plurality of segments to enable removal of said plurality of segments from said curved guide and replacement with a number of new linked segments.

2. The apparatus of claim 1, wherein each linked segment further has a second cutting surface.

3. The apparatus of claim 2, wherein each linked segment is defined by a generally cylindrical body, and said cutting surfaces are disposed diametrically opposite each other on said cylindrical body.

4. The apparatus of claim 1, wherein said curved guide comprises a rod.

5. The apparatus of claim 1, wherein said linked segments are coupled to each other in a manner allowing axial displacement of said linked segments relative to one another.

6. The apparatus of claim 5, wherein each linked segment includes:
   a concavity on one end thereof; and
   a convexity on another end thereof;
   said concavity and said convexity being complementary in structure.

7. The apparatus of claim 1, wherein a last segment of said linked segments is configured to be rotatably received in said frame.

8. An apparatus for milling bone comprising:
   a frame;
   a curved guide supported by said frame;
   a reamer rotatably maintained on said curved guide, said reamer comprising:
   a first segment;
   a last segment configured to be rotatably received in a milling frame: and
   a plurality of intermediate segments defining a first end that is linked to said first segment and a second end that is linked to said last segment, each intermediate segment having a first cutting surface; and
   a universal joint in communication with said first segment and configured to be coupled to a source of rotary motions,
   wherein said universal joint comprises a drive connector that is removably coupled to said first segment whereby said drive connector may be decoupled from said first segment.

9. The apparatus of claim 8, wherein each intermediate segment has a second cutting surface.

10. The apparatus of claim 9, wherein each intermediate segment is defined by a generally cylindrical body, and said first and second cutting surfaces are disposed diametrically opposite each other on said cylindrical body.

11. The apparatus of claim 8, wherein each intermediate segment is rotatably retained on said curved guide.

12. The apparatus of claim 11, wherein each intermediate segment includes a bore defining an axis of rotation and said curved guide extends through said bores.

13. The apparatus of claim 8, wherein said intermediate segments are linked to each other in a manner allowing axial displacement relative to one another.

14. The apparatus of claim 13, wherein each intermediate segment includes:
- a concavity on one end thereof; and
- a convexity on another end thereof;
- said concavity and said convexity being complementary in structure.

* * * * *